(12) United States Patent
Numazu

(10) Patent No.: US 9,147,241 B2
(45) Date of Patent: Sep. 29, 2015

(54) GLASS BOTTLE INSPECTION METHOD AND APPARATUS

(75) Inventor: Masaaki Numazu, Kawasaki (JP)

(73) Assignee: KIRIN TECHNO-SYSTEM COMPANY, LIMITED, Kanagawa (JP)

( * ) Notice: Subject to any disclaimer, the term of this patent is extended or adjusted under 35 U.S.C. 154(b) by 113 days.

(21) Appl. No.: 14/125,352

(22) PCT Filed: Jun. 15, 2011

(86) PCT No.: PCT/JP2011/064186
§ 371 (c)(1),
(2), (4) Date: Dec. 11, 2013

(87) PCT Pub. No.: WO2012/172695
PCT Pub. Date: Dec. 20, 2012

(65) Prior Publication Data
US 2014/0119634 A1    May 1, 2014

(51) Int. Cl.
G06K 9/00 (2006.01)
G06T 7/00 (2006.01)
G01N 21/90 (2006.01)

(52) U.S. Cl.
CPC .............. G06T 7/001 (2013.01); G01N 21/90 (2013.01); G01N 21/9036 (2013.01); G01N 21/9054 (2013.01)

(58) Field of Classification Search
USPC ......... 382/141, 143, 149, 152; 348/86, 95, 25
See application file for complete search history.

(56) References Cited

U.S. PATENT DOCUMENTS

| | | | |
|---|---|---|---|
| 6,448,549 B1 * | 9/2002 | Safaee-Rad | ............... 250/223 B |
| 6,480,280 B1 | 11/2002 | Hinata | |
| 6,536,294 B1 * | 3/2003 | Pemberton et al. | .......... 73/865.8 |
| 6,618,495 B1 * | 9/2003 | Furnas | ........................... 382/142 |
| 7,329,855 B2 * | 2/2008 | Katayama et al. | ......... 250/223 B |
| 7,330,251 B2 * | 2/2008 | Katayama et al. | ......... 356/240.1 |
| 7,626,158 B2 * | 12/2009 | Diehr et al. | ............... 250/223 B |
| 7,781,723 B1 * | 8/2010 | Furnas | ...................... 250/223 B |
| 2005/0069191 A1 | 3/2005 | Van Der Meer et al. | |
| 2006/0000968 A1 | 1/2006 | Katayama et al. | |
| 2006/0045324 A1 | 3/2006 | Katayama et al. | |
| 2008/0093538 A1 | 4/2008 | Diehr et al. | |

FOREIGN PATENT DOCUMENTS

| | | |
|---|---|---|
| EP | 0 483 966 A2 | 5/1992 |
| JP | 58-744 A | 1/1983 |

(Continued)

OTHER PUBLICATIONS

Extended European Search Report dated Feb. 20, 2015, issued by the European Patent Office in counterpart European application No. 11868002.4.

*Primary Examiner* — Yosef Kassa
(74) *Attorney, Agent, or Firm* — Sughrue Mion, PLLC

(57) ABSTRACT

The glass bottle inspection method and apparatus performs successively producing differential images from original images successively captured from the glass bottle to be inspected while the glass bottle is being rotated about its own axis, comparing the differential images with the template to judge whether the glass bottle is defect-free or not, and combining all the differential images obtained from the glass bottle to be inspected in one inspection cycle to produce a differential composite image, using the differential composite image as a provisional template when all the differential images obtained from the glass bottle in one inspection cycle are judged as representing a defect-free glass bottle, and correcting the template using the provisional template.

10 Claims, 11 Drawing Sheets

(56) References Cited

FOREIGN PATENT DOCUMENTS

| | | |
|---|---|---|
| JP | 63-277960 A | 11/1988 |
| JP | 11-108854 A | 4/1999 |
| JP | 2002-357558 A | 12/2002 |
| JP | 2002-357559 A | 12/2002 |
| JP | 4478786 B2 | 6/2010 |
| WO | 2004/036197 A1 | 4/2004 |
| WO | 2004/036198 A1 | 4/2004 |
| WO | 2004/036199 A1 | 4/2004 |

* cited by examiner

FIG. 13
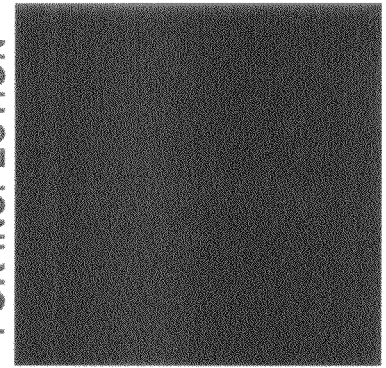
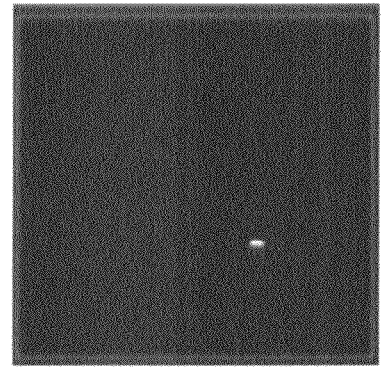
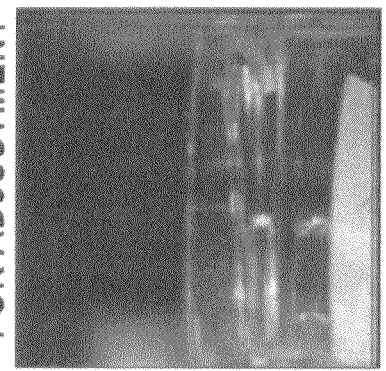
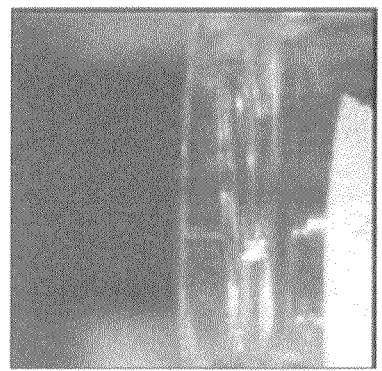

DIFFERENTIAL
COMPOSITE IMAGE

GLASS BOTTLE INSPECTION METHOD AND APPARATUS

CROSS REFERENCE TO RELATED APPLICATIONS

This application is a National Stage of International Application No. PCT/JP2011/064186 filed Jun. 15, 2011, the contents of all of which are incorporated herein by reference in their entirety.

TECHNICAL FIELD

The present invention relates to a glass bottle inspection method and apparatus, and more particularly to a glass bottle inspection method and apparatus for detecting a defect at a specific location of a bottle-mouth portion and the like of a glass bottle by an imaging process.

BACKGROUND ART

In producing a glass bottle, a crack such as crazing may be sometimes formed in a wall thickness of a bottle-mouth portion. This crack is referred to as a check. Glass bottles tend to have checks in limited regions of the bottle-mouth portions. Typically, there are a check generated in the top surface or near the top surface of the bottle mouth, a check generated in a screw thread portion of the bottle mouth, and a check generated in a skirt portion of the bottle mouth. Further, depending on the direction of the crack, the checks are classified into a vertical check extending in a vertical direction (substantially vertical direction) and a lateral check extending in a lateral direction (substantially horizontal direction).

Because the above-mentioned check can cause damage to the glass bottle, the presence or absence of a check is detected by imaging the bottle-mouth portion, and the glass bottle having the check is removed as a defective bottle.

Heretofore, there has been known a glass bottle inspection apparatus for automatically inspecting a glass bottle by imaging a bottle-mouth portion of a glass bottle to detect whether there is a check or not. The known glass bottle inspection apparatus has a single illuminating unit disposed above a bottle-mouth portion of a glass bottle and a number of (e.g., seven) cameras disposed around the bottle-mouth portion so as to surround the bottle-mouth portion. Scattered light emitted from the illuminating unit is applied to the bottle-mouth portion of the glass bottle, and if there is a check, the light is reflected by a crack plane of the check and is thus illuminated brightly. Therefore, images captured by the cameras include a brighter image area corresponding to the check than other image areas.

CITATION LIST

Patent Literature

Patent document 1: Japanese Patent No. 4478786

SUMMARY OF INVENTION

Technical Problem

In the case where the bottle-mouth portion of the glass bottle is inspected to detect whether there is a check or not, it is considered that a template matching process for producing a template serving as a reference image based on the previously captured images of defect-free glass bottles, acquiring images of the glass bottle to be inspected, and comparing the acquired images with the template to judge whether the glass bottle is defect-free or not is used.

It has been the practice for a glass bottle manufacturing factory to manufacture glass bottles using a plurality of molds. Even though the molds have essentially no dimensional accuracy discrepancies, the molds are required to be coated with a mold release agent to allow the products to be easily released therefrom. If the mold release agent is applied in various amounts to the molds and the molds are regulated to various temperatures, those variations are liable to adversely affect images captured by CCD cameras, thus possibly causing a glass bottle that should be judged as defect-free to be judged as a defective glass bottle.

It is thus necessary for the glass bottle manufacturing factory to review the reference image (template) depending on the operational status. Specifically, the template is required to cope with the operational status in the production line because it is not proper that once the template is produced, attention should be paid only to its own reproducibility. Consequently, it is necessary for the glass bottle manufacturing factory to update the template by adding the data of newly manufactured glass bottles to the template produced beforehand based on the data of the defect-free glass bottles while manufacturing glass bottles. In this case, the glass bottle manufacturing factory produces a large number of glass bottles per unit time, and thus the glass bottle inspection apparatus that is expensive is required to have a high-throughput performance in which a large number of glass bottles can be inspected by a single apparatus. Therefore, the glass bottle inspection apparatus needs to perform an inspection of checks at a high speed and also to add the data to the template at a high speed. For example, a glass bottle inspection apparatus is required to have a processing capability of at least 200 BPM (Bottles Per Minute), and to capture and process about 200 to 400 images for the inspection of one glass bottle. In the case where glass bottles are required to be processed at a rate of at least 200 BPM, the glass bottle inspection apparatus needs to inspect at least 3.3 bottles in one second. Therefore, the number of images to be captured and processed becomes 660 to 1320 images in one second. Consequently, if the template matching process is applied to a glass bottle manufacturing factory or the like, the template production and the inspection of checks are required to be performed simultaneously, and when there is a defective bottle with a check, the data of the check itself are added as template data.

The present invention has been made in view of the above problems. It is therefore an object of the present invention to provide a glass bottle inspection method and apparatus, which are capable of producing a template serving as a reference image based on previously captured images of defect-free glass bottles, acquiring images of the glass bottle to be inspected, and comparing the acquired images with the template to judge whether the glass bottle is defect-free or not at a high speed, and which are also capable of adding only the image data of a glass bottle judged as a defect-free glass bottle after it has been inspected, to the template serving as the reference image, thereby correcting or updating the template.

Solution to Problem

In order to achieve the above object, according to a first aspect of a glass bottle inspection method of the present invention, there is provided a glass bottle inspection method for detecting a defect at a specific location of a glass bottle by producing a template serving as a reference image based on images of a defect-free glass bottle which have been captured previously using an illuminating unit and a camera, and by comparing an image of the glass bottle to be inspected with the template, the glass bottle inspection method comprising: successively producing differential images from original images which are successively captured from the glass bottle to be inspected while the glass bottle is being rotated about its own axis; comparing the differential images with the template to judge whether the glass bottle is defect-free or not, and combining all the differential images obtained from the glass bottle to be inspected in one inspection cycle to produce a differential composite image; using the differential composite image as a provisional template when all the differential images obtained from the glass bottle in one inspection cycle are judged as representing a defect-free glass bottle; and correcting the template using the provisional template.

According to the present invention, a template serving as a reference image is produced based on images of a defect-free glass bottle which have been captured previously using an illuminating unit and a camera. Differential images are successively produced, each from two original images successively captured from the glass bottle while the glass bottle is being rotated about its own axis. The differential images are compared with the template to judge whether the glass bottle is defect-free or not, and all the differential images produced from the glass bottle to be inspected in one inspection cycle are combined to produce a differential composite image. Then, the differential composite image is used as a provisional template if all the differential images produced from the glass bottle in one inspection cycle are judged as representing a defect-free glass bottle. Since the provisional template is produced from the images of the defect-free glass bottle, the provisional template can be combined as additional data with the template which has been used in the previous inspection process. On the other hand, if the differential composite image which is produced in one inspection cycle represents a defective bottle, i.e., if any one of the differential images produced in one inspection cycle is judged as representing a defective bottle in the process of comparing the differential images and the template, then the differential composite image is not used as a provisional template. Consequently, if the present invention is used in a glass bottle manufacturing factory, while glass bottles are being manufactured, the data of defect-free glass bottles that are newly manufactured may be added to the template that has been produced beforehand based on a defect-free glass bottle, thereby correcting or updating the template. Thus, the template (image) that copes with the operational status in the production line can be produced.

According to a second aspect of a glass bottle inspection method of the present invention, there is provided a glass bottle inspection method for detecting a defect at a specific location of a glass bottle by producing a template serving as a reference image based on images of a defect-free glass bottle which have been captured previously using an illuminating unit and a camera, and by comparing an image of the glass bottle to be inspected with the template, the glass bottle inspection method comprising: judging whether the glass bottle is defect-free or not by comparing original images which are successively captured from the glass bottle to be inspected while the glass bottle is being rotated about its own axis or comparative images produced from the original images, with the template, and combining all the original images or all the comparative images obtained from the glass bottle to be inspected in one inspection cycle to produce a composite image; using the composite image as a provisional template when all the original images or all the comparative images obtained from the glass bottle in one inspection cycle are judged as representing a defect-free glass bottle; and correcting the template using the provisional template.

According to the present invention, a template serving as a reference image is produced based on images of a defect-free glass bottle which have been captured previously using an illuminating unit and a camera. Then, whether the glass bottle is defect-free or not is judged by comparing original images which are successively captured from the glass bottle to be inspected while the glass bottle is being rotated about its own axis or comparative images produced from the original images, with the template, and all the original images or all the comparative images obtained from the glass bottle to be inspected in one inspection cycle are combined to produce a composite image. Then, the composite image is used as a provisional template if all the original images or all the comparative images obtained from the glass bottle in one inspection cycle are judged as representing a defect-free glass bottle. Since the provisional template is produced from the images of the defect-free glass bottle, the provisional template can be combined as additional data with the template which has been used in the previous inspection process. On the other hand, if the composite image which is produced in one inspection cycle represents a defective bottle, i.e., if any one of the original images or the comparative images obtained in one inspection cycle is judged as representing a defective bottle in the process of comparing the original images or the comparative images with the template, then the composite image is not used as a provisional template and is not combined. Consequently, if the present invention is used in a glass bottle manufacturing factory, while glass bottles are being manufactured, the data of defect-free glass bottles that are newly manufactured may be added to the template that has been produced beforehand based on a defect-free glass bottle, thereby correcting or updating the template. Thus, the template (image) that copes with the operational status in the production line can be produced.

In a preferred aspect of the present invention, the template is produced by successively producing differential images from original images which are successively captured from a predetermined number of defect-free glass bottles, and by superposing the produced differential images.

According to the present invention, differential images are successively produced from original images which are successively captured from defect-free glass bottles. Specifically, an original image that has been captured and an original image that has been captured at a next timing are superposed one on the other, the pixel values of one of the images are subtracted from the pixel values of the other image, and the absolute values of the differences are used as the pixel values of a differential image. Then, the generated differential images are superposed to produce a template.

In a preferred aspect of the present invention, the template is corrected by combining the provisional template as additional data with the template.

In a preferred aspect of the present invention, the defect at the specific location of the glass bottle comprises a check in the bottle-mouth portion.

According to a first aspect of a glass bottle inspection apparatus of the present invention, there is provided a glass bottle inspection apparatus for detecting a defect at a specific location of a glass bottle by producing a template serving as a reference image with an image processor which processes images of a defect-free glass bottle which have been captured previously using an illuminating unit and a camera, and by comparing an image of the glass bottle to be inspected with the template, wherein the image processor is configured to perform: successively producing differential images from original images which are successively captured from the glass bottle to be inspected while the glass bottle is being rotated about its own axis; comparing the differential images with the template to judge whether the glass bottle is defect-free or not, and combining all the differential images obtained from the glass bottle to be inspected in one inspection cycle to produce a differential composite image; using the differential composite image as a provisional template when all the differential images obtained from the glass bottle in one inspection cycle are judged as representing a defect-free glass bottle; and correcting the template using the provisional template.

According to a second aspect of a glass bottle inspection apparatus of the present invention, there is provided a glass bottle inspection apparatus for detecting a defect at a specific location of a glass bottle by producing a template serving as a reference image with an image processor which processes images of a defect-free glass bottle which have been captured previously using an illuminating unit and a camera, and by comparing an image of the glass bottle to be inspected with the template, wherein the image processor is configured to perform: judging whether the glass bottle is defect-free or not by comparing original images which are successively captured from the glass bottle to be inspected while the glass bottle is being rotated about its own axis or comparative images produced from the original images, with the template, and combining all the original images or all the comparative images obtained from the glass bottle to be inspected in one inspection cycle to produce a composite image; using the composite image as a provisional template when all the original images or all the comparative images obtained from the glass bottle in one inspection cycle are judged as representing a defect-free glass bottle; and correcting the template using the provisional template.

In a preferred aspect of the present invention, the template is produced by successively producing differential images from original images which are successively captured from a predetermined number of defect-free glass bottles, and by superposing the generated differential images.

In a preferred aspect of the present invention, the template is corrected by combining the provisional template as additional data with the template.

In a preferred aspect of the present invention, the defect at the specific location of the glass bottle comprises a check in the bottle-mouth portion.

Advantageous Effects of Invention

The present invention offers the following effects.

(1) A template serving as a reference image is produced based on previously captured images of a defect-free glass bottle, and images of the glass bottle to be inspected are acquired. The acquired images are compared with the template to judge whether the glass bottle is defect-free or not at a high speed.

(2) Only the image data of a glass bottle judged as a defect-free glass bottle after it has been inspected are added to the template serving as the reference image, thereby correcting or updating the template.

(3) Differential images are successively produced from original images which are successively captured from the glass bottle to be inspected while the glass bottle is being rotated about its own axis. The differential images are compared with the template to judge whether the glass bottle is defect-free or not, and all the differential images produced from the glass bottle to be inspected in one inspection cycle are combined to produce a differential composite image. Though the differential image and the template image have entirely different shapes, the differential composite image and the template have substantially the same shape, and thus a characteristic inspection such as an area calculation or a circumferential length can be performed.

BRIEF DESCRIPTION OF DRAWINGS

FIG. 13 shows original images for adjustment and original images for inspection by way of example;

DESCRIPTION OF EMBODIMENTS

A glass bottle inspection method and apparatus according to embodiments of the present invention will be described below with reference to FIGS. 1 through 15. In the glass bottle inspection method and apparatus according to the present invention, a bottle-mouth portion of a glass bottle will be described as a specific location of the glass bottle to be inspected, and a check in the bottle-mouth portion will be described as a defect to be inspected.

A glass bottle to be inspected is held by an inspection star wheel (not shown) and is conveyed along a conveyance path on a circumference of the star wheel. The glass bottle inspection apparatus according to the present invention is disposed in one inspecting station at a certain place in the conveyance path on the circumference of the star wheel. The glass bottle conveyed by the start wheel is indexed to the inspecting station, where the presence or absence of a check in the bottle-mouth portion of the glass bottle is inspected by the glass bottle inspection apparatus according to the present invention.

Figure 1:
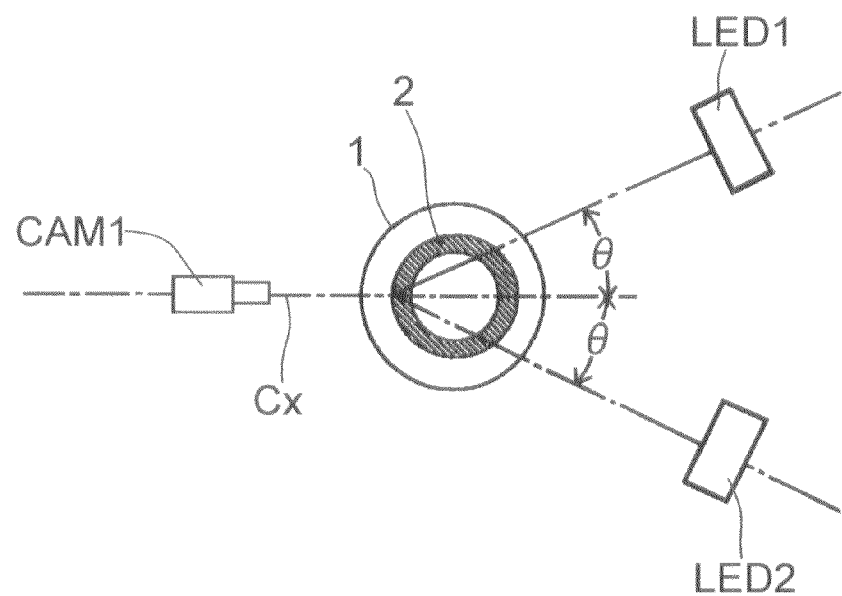
FIG. 1 is a plan view showing a glass bottle inspection apparatus.

FIG. 1 is a plan view of the glass bottle inspection apparatus. As shown in FIG. 1, the glass bottle inspection apparatus has two illuminating units LED1, LED2 and a single camera CAM1 which are disposed around the bottle-mouth portion 2 of a glass bottle 1. The bottle-mouth portion 2 is shown by oblique lines in FIG. 1. The illuminating units LED1 and LED2 are disposed at the opposite side of the camera CAM 1 across the glass bottle 1 to be inspected. The illuminating units LED1 and LED2 are disposed in laterally symmetrical positions with respect to an optical axis Cx of the camera CAM1. Therefore, regardless of whether light from the illuminating units LED1 and LED2 is reflected to the right or left by a crack plane of a check, the light can be imaged by the camera CAM1. The illuminating units LED1 an LED2 comprise a red LED, and the camera CAM1 comprises a CCD camera.

Figure 2:
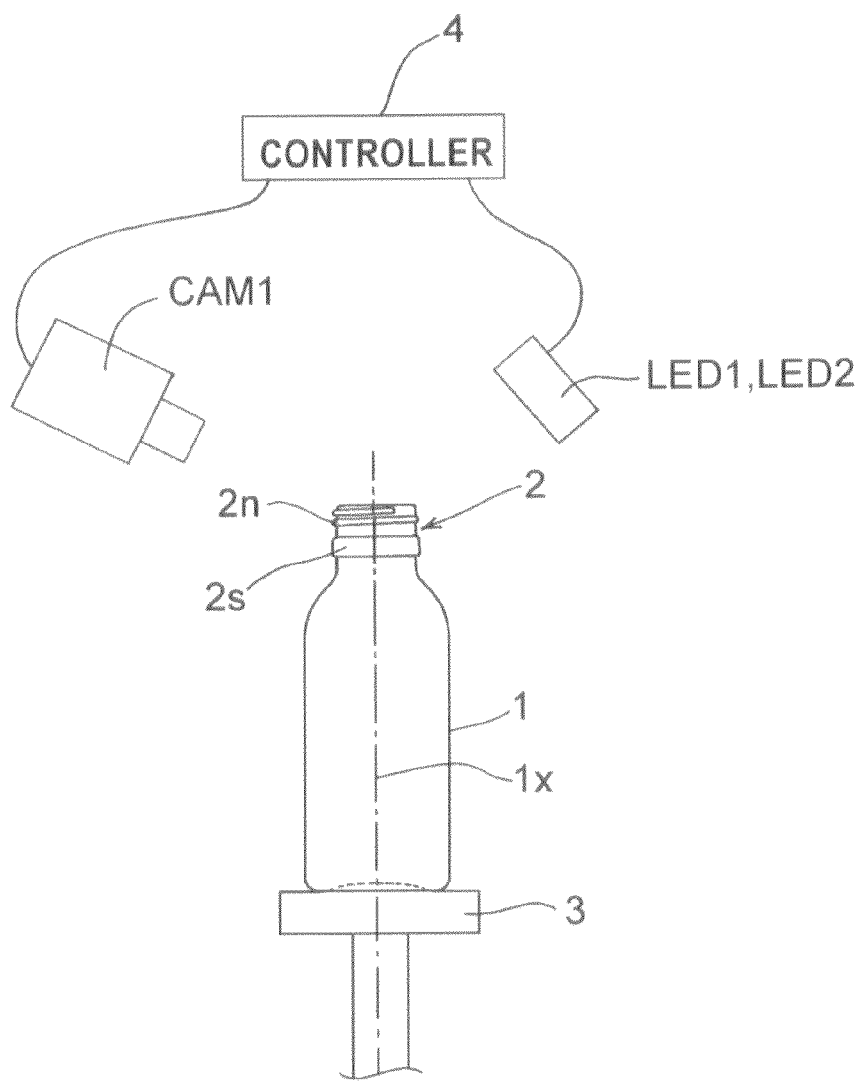
FIG. 2 is an elevational view showing the glass bottle inspection apparatus.

FIG. 2 is an elevational view showing the glass bottle inspection apparatus. As shown in FIG. 2, the glass bottle 1 is placed on a bottle support 3. When the bottle support 3 is rotated about its own axis, the glass bottle 1 is rotated about its own axis 1x. The bottle-mouth portion 2 of the glass bottle 1 has a thread 2n and a skirt 2s below the thread 2n. The illuminating units LED1 and LED2 are disposed obliquely upwardly of the bottle-mouth portion 2 of the glass bottle 1. The camera CAM1 is disposed obliquely upwardly of the bottle-mouth portion 2 of the glass bottle 1.

The illuminating units LED1 and LED2 and the camera CAM1 are connected to a controller 4. The illuminating units LED1 and LED2 are controlled by the controller 4 to emit alternate pulsed lights, and the camera CAM1 is controlled by the controller 4 to capture images of the bottle-mouth portion 2 in synchronism with the pulsed lights from the illuminating units LED1 and LED2. Specifically, the image capturing timing of the camera CAM1 is established in synchronism with the pulsed light from the illuminating unit LED1, and the image capturing timing of the camera CAM1 is established in synchronism with the pulsed light from the illuminating unit LED2. The controller 4 includes an image processor for processing images captured by the camera CAM1. Therefore, the images captured by the camera CAM1 are processed by the image processor.

Figure 3:
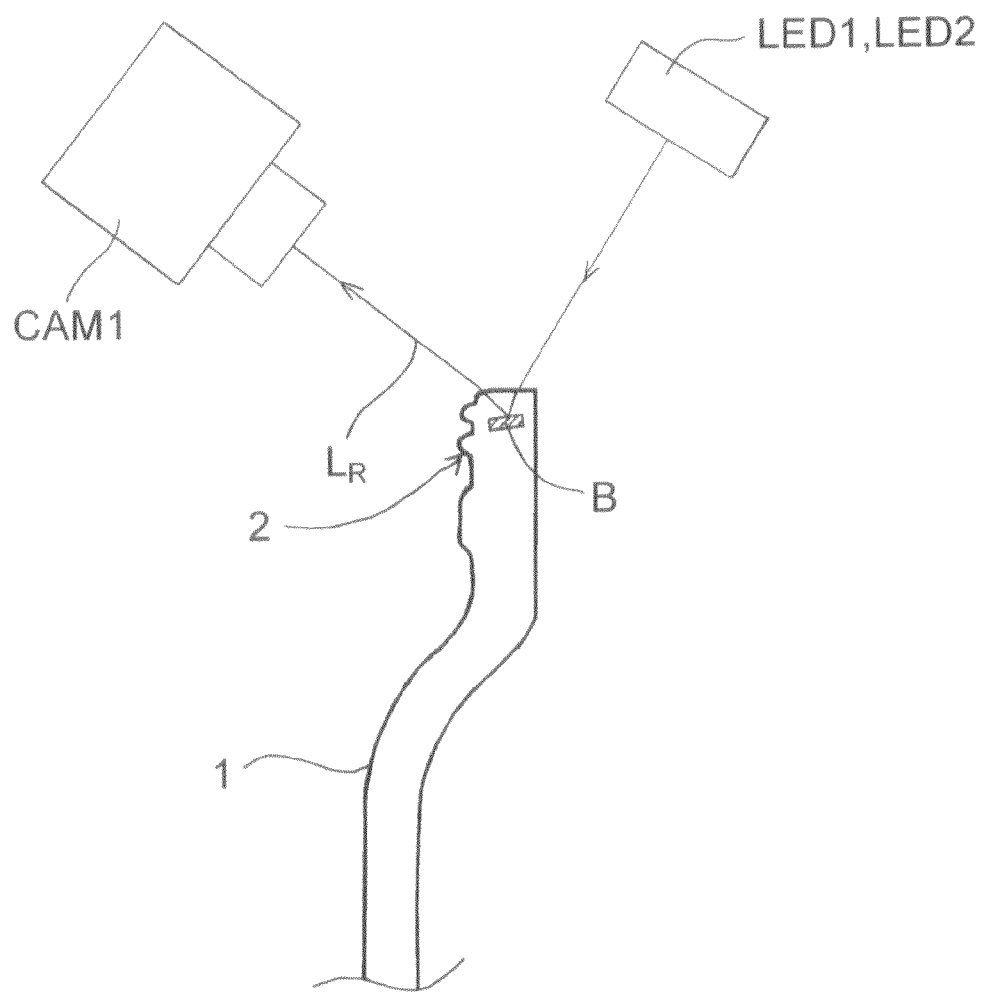
FIG. 3 is a schematic elevational view showing a light path in which light is emitted from an illuminating unit LED1 or an illuminating unit LED2 and applied to a bottle-mouth portion of a glass bottle, and light from the bottle-mouth portion is captured by a camera.
Figure 4:
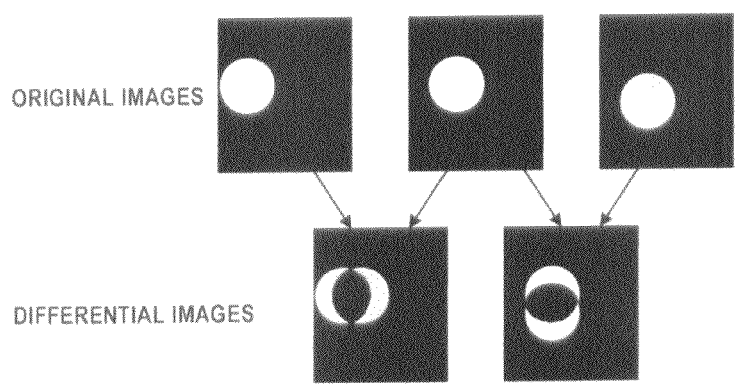
FIG. 4 is a schematic diagram illustrating an inspecting procedure of the glass bottle inspection apparatus according to the present invention.

FIG. 3 is a schematic elevational view showing a light path in which light is emitted from the illuminating unit LED1 or LED2 and applied to the bottle-mouth portion 2 of the glass bottle 1, and light from the bottle-mouth portion 2 is captured by the camera CAM1. As shown in FIG. 3, the light that is emitted from the illuminating unit LED1 or LED2 is applied to the bottle-mouth portion 2 of the glass bottle 1. If the bottle-mouth portion 2 has a check B, then the light applied to the bottle-mouth portion 2 is reflected by the crack plane of the check B. The reflected light $L_R$ is imaged by the camera CAM1. In an image captured by the camera CAM1, an image area corresponding to the check is brighter than other image areas of the image.

An inspecting procedure of the glass bottle inspection apparatus having the above structure will be described below with reference to FIGS. 4 through 11. In FIGS. 4 through 11, each image is schematically illustrated.

(1) Production Process of a New Template:

First, a process of producing a new template by capturing the images of a predetermined number of defect-free bottles will be described below. Light from the illuminating unit LED1 or LED2 enters the bottle-mouth portion 2 of the bottle 1 placed on the bottle support 3 from above the bottle-mouth portion 2. The light that has entered the bottle-mouth portion 2 is transmitted through and/or reflected by the bottle-mouth portion 2, and captured by the camera CAM1 that is disposed obliquely upwardly of the bottle-mouth portion 2. At this time, the camera CAM1 captures a number of successive original images of the bottle-mouth portion 2 while the glass bottle 1 is being rotated about its own axis by the bottle support 3. Concurrently with the above image capturing process, the image processor provided in the controller 4 successively produces differential images each from two original images that have been successively captured. Specifically, an original image that has been captured and an original image that has been captured at a next timing are superposed one on the other, the pixel values of one of the images are subtracted from the pixel values of the other image, and the absolute values of the differences are used as the pixel values of a differential image. In this case, a number of differential images are produced from successive original images captured from the entire circumference of the bottle-mouth portion 2. For example, about 200 to 400 differential images are produced in one inspection cycle.

Figure 5:
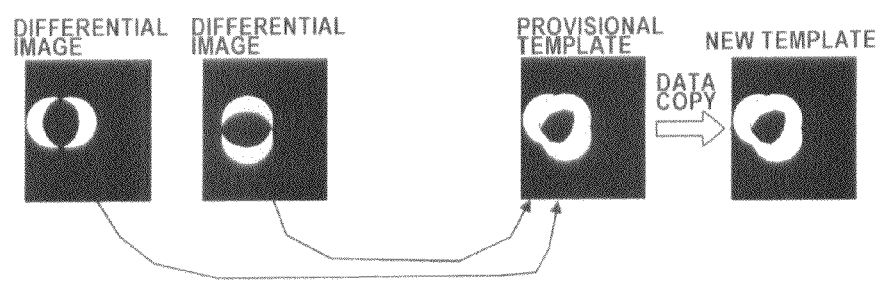
FIG. 5 is a schematic diagram illustrating an inspecting procedure of the glass bottle inspection apparatus according to the present invention.

Then, as shown in FIG. 5, a provisional template is produced from the differential images. In this case, the image processor superposes some differential images and prioritizes brighter pixels at all times, thereby producing pixel values from the brighter pixels. The provisional template is produced until a specified condition is met (until a certain number of, e.g., 50, bottles are inspected). When the template producing condition is met (when the certain number of bottles are inspected), the data of the provisional template are copied to the template to be used for inspection, thereby producing a new template based on only the predetermined number of defect-free bottles. It has been described above that a new template is produced from a predetermined number of defect-free bottles. However, a new template may be produced from original images which are captured from a number of defect-free bottles within a predetermined period of time. In other words, the template producing condition may be a number of bottles to be inspected or an inspection time.

(2) Inspection of a Glass Bottle using a New Template:

A glass bottle that is actually manufactured by a glass bottle manufacturing process is inspected using a new template produced from defect-free bottles.

Figure 6:
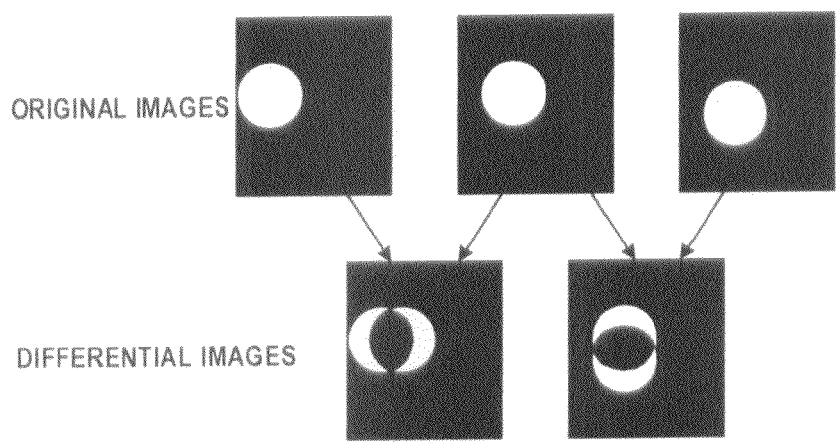
FIG. 6 is a schematic diagram illustrating an inspecting procedure of the glass bottle inspection apparatus according to the present invention.

The glass bottle inspection apparatus shown in FIG. 2 captures a number of successive original images of a bottle-mouth portion 2 of a glass bottle 1 to be inspected while rotating the glass bottle 1 about its own axis. Concurrently with the image capturing process, the image processor provided in the controller 4 successively produces differential images each from two original images that have been successively captured, as shown in FIG. 6. Specifically, an original image that has been captured and an original image that has been captured at a next timing are superposed one on the other, the pixel values of one of the images are subtracted from the pixel values of the other image, and the absolute values of the differences are used as the pixel values of a differential image. For example, about 200 to 400 differential images are produced in one inspection cycle.

Then, the image processor compares the differential images with the new template. The image processor judges that the glass bottle is a defect-free glass bottle with the bottle-mouth portion 2 being free of a check if a differential image is composed of pixel values darker than the template, and judges that the glass bottle is a defective glass bottle with the bottle-mouth portion 2 having a check if a differential image includes pixel values brighter than the template. While one glass bottle is being inspected, differential images are successively produced, and each time a differential image is produced, the differential image is compared with the template to make the above judgment.

Figure 8:
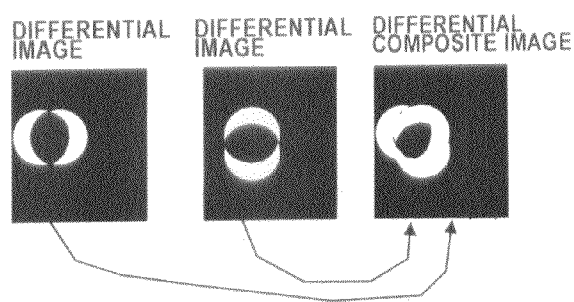
FIG. 8 is a schematic diagram illustrating an inspecting procedure of glass bottle inspection apparatus according to the present invention.
Figure 9:
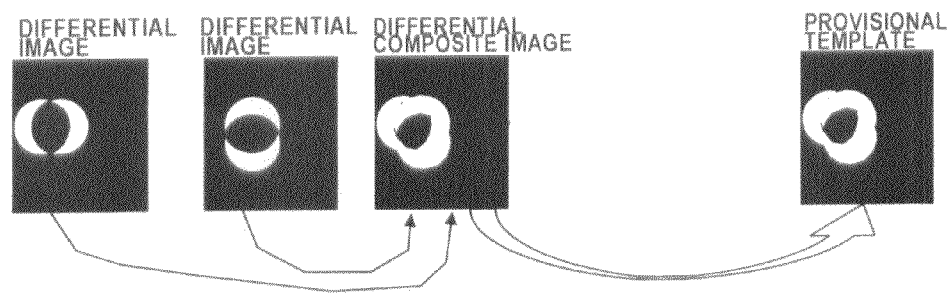
FIG. 9 is a schematic diagram illustrating an inspecting procedure of the glass bottle inspection apparatus according to the present invention.

At the same time that the image processor makes the above judgment by comparing the differential images with the template, the image processor combines the produced differential images sequentially. In this manner, as shown in FIG. 8, the differential images (a number of differential images produced from the original images successively captured from the glass bottle) produced in one inspection cycle are combined to produce a differential composite image. For example, about 200 to 400 differential images produced in one inspection cycle are combined to produce a differential composite image.

Figure 7:
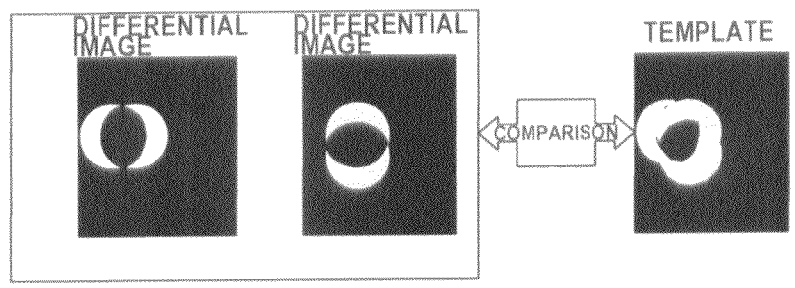
FIG. 7 is a schematic diagram illustrating an inspecting procedure of the glass bottle inspection apparatus according to the present invention.
Figure 10:
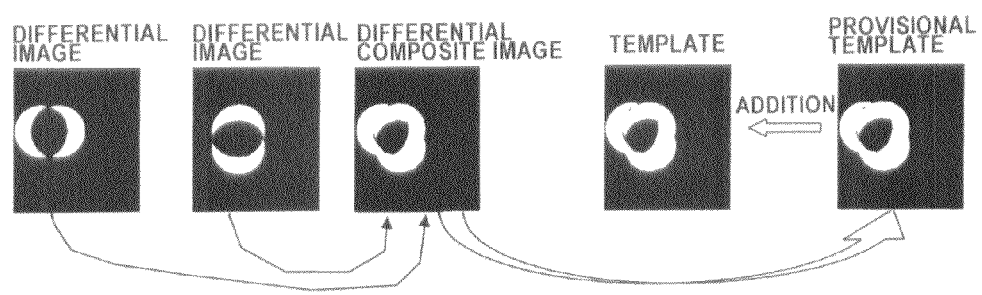
FIG. 10 is a schematic diagram illustrating an inspecting procedure of the glass bottle inspection apparatus according to the present invention.

(3) Updating of a Template:

If the differential composite image shown in FIG. 8 which is produced in one inspection cycle represents a defect-free bottle, i.e., if all the differential images produced in one inspection cycle are judged as representing a defect-free bottle in the comparison process shown in FIG. 7, then the image processor uses the differential composite image as a provisional template. On the other hand, if the differential composite image which is produced in one inspection cycle represents a defective bottle, i.e., if any one of the differential images produced in one inspection cycle is judged as representing a defective bottle in the comparison process shown in FIG. 7, then the image processor does not use the differential composite image as a provisional template. The provisional template produced from the defect-free bottle is combined as additional data with the template which has been used in the previous inspection process, as shown in FIG. 10. When the provisional template is combined as additional data, it may be processed and then combined, or it may be combined as it is. Consequently, if the present invention is used in a glass bottle manufacturing factory, while glass bottles are being manufactured, the data of defect-free glass bottles that are newly manufactured may be added to the template that has been produced beforehand based on defect-free glass bottles, thereby correcting or updating the template. Thus, the template (image) that copes with the operational status in the production line can be produced. A next glass bottle can be inspected using the corrected or updated template.

Figure 11:
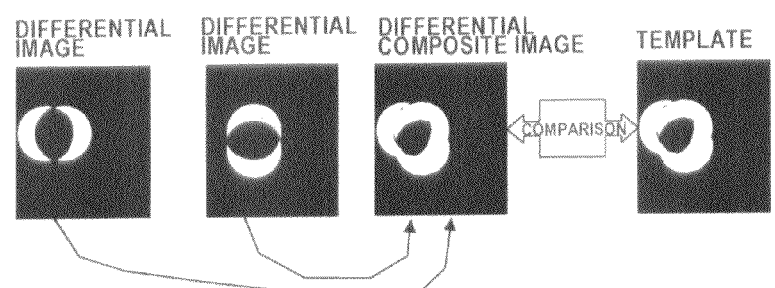
FIG. 11 is a schematic diagram illustrating an inspecting procedure of the glass bottle inspection apparatus according to the present invention.

As shown in FIG. 11, the produced differential composite image and the template may be compared with each other to perform a characteristic inspection such as an area calculation or a circumferential length. Though the differential image and the template image have entirely different shapes, the differential composite image and the template have substantially the same shape, and thus the characteristic inspection such as an area calculation or a circumferential length can be performed.

Figure 12:
FIG. 12 shows a captured image of the bottle-mouth portion of the glass bottle to be inspected.
Figure 14:
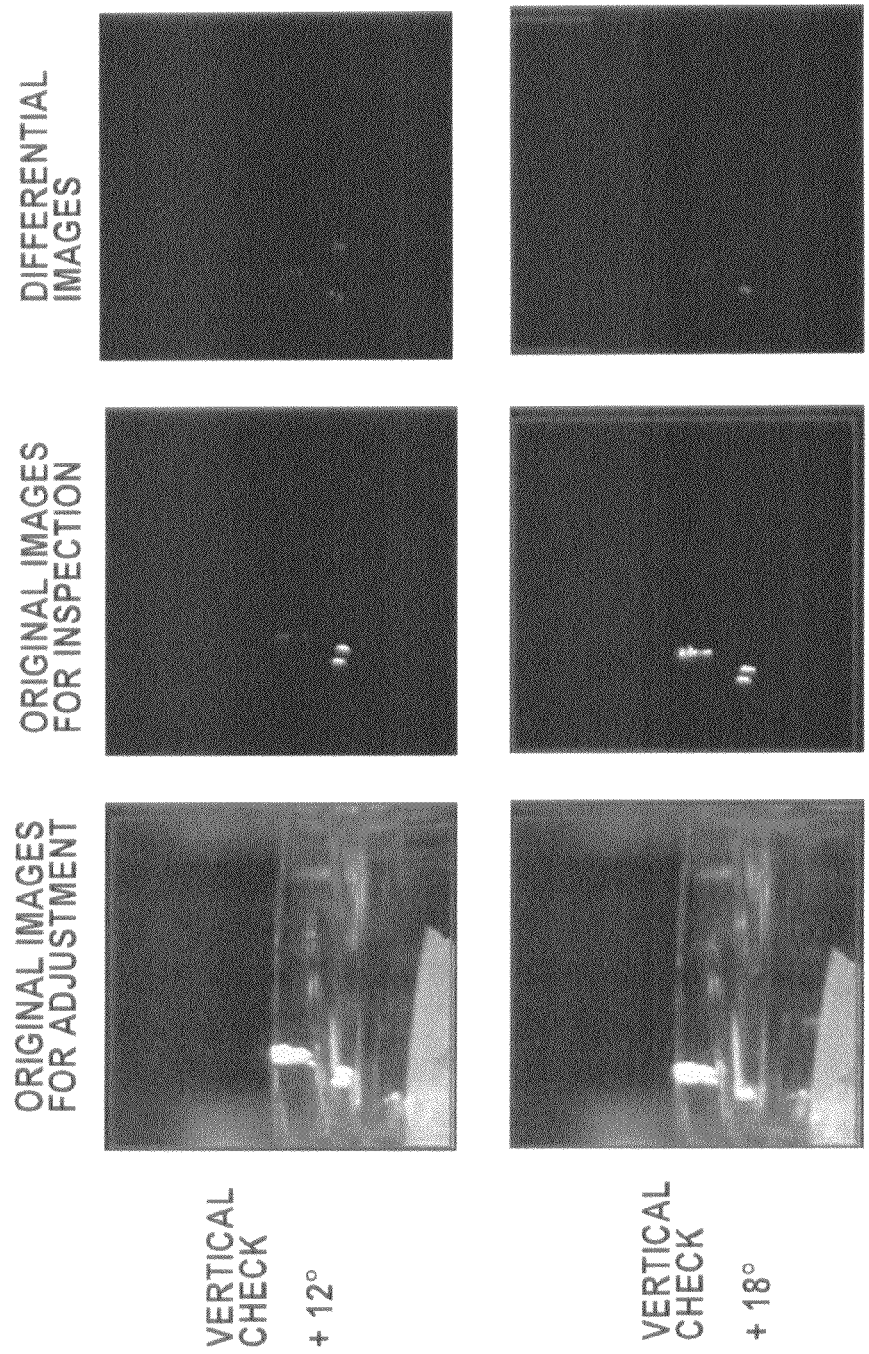
FIG. 14 shows original images for adjustment, original images for inspection, and differential images by way of example.

FIGS. 12 through 15 show images that are acquired in an actual process of inspecting glass bottles. FIG. 12 shows a captured image of a bottle-mouth portion of a glass bottle to be inspected. FIG. 13 shows original images for adjustment and original images for inspection by way of example. FIG. 14 shows original images for adjustment, original images for inspection, and differential images by way of example.

Figure 15:
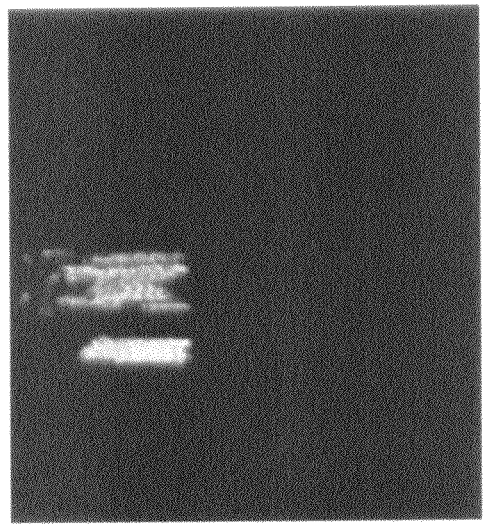
FIG. 15 shows a differential composite image by way of example.

In FIGS. 13 and 14, the original images for adjustment are images captured from a glass bottle having a vertical check. The vertical check changes its position as the glass bottle rotates about its own axis. In FIG. 13, the upper images are images captured when the vertical check is on the front side, and the lower images are images captured when the vertical check is moved by +6° from the front side. In FIG. 14, the upper images are images captured when the vertical check is moved by +12° from the front side, and the lower images are images captured when the vertical check is moved by +18° from the front side. FIG. 15 shows a differential composite image by way of example.

In the embodiment shown in FIGS. 1 through 15, differential images are produced from the original images, and the differential images are compared with the template to judge whether the glass bottle is defect-free or not. However, if the original images can directly be compared with the template, the original images may be compared with the template to judge whether the glass bottle is defect-free or not. Alternatively, comparative images that are different in form from the differential images may be produced from the original images, and the comparative images are compared with the template to judge whether the glass bottle is defect-free or not. In this case, the comparative images are combined to produce a composite image.

Further, in the embodiment shown in FIGS. 1 through 15, the case where a check is detected in the bottle-mouth portion of the glass bottle has been described. However, the present invention may be applied to the detection of a check in regions other than the bottle-mouth portion of a glass bottle, e.g., in the bottom of the glass bottle. Further, some glass bottles are manufactured as returnable bottles that are retrieved for reuse after they have been used. Returnable bottles are likely to have checks at their bottle-mouth portions when they are brought into contact with each other or with other objects while in use or transport. The present invention is also applicable to the inspection of a check in the returnable bottle.

Although the embodiments of the present invention have been described above, the present invention is not limited to the above embodiments, but may be reduced to practice in various different configurations within the scope of the technical concept thereof.

INDUSTRIAL APPLICABILITY

The present invention is applicable to a glass bottle inspection method and apparatus for detecting a defect at a specific location such as a bottle-mouth portion of a glass bottle by an imaging process.

REFERENCE SIGNS LIST

1 Glass bottle
2 Bottle-mouth portion
$2n$ Thread
$2s$ Skirt
3 Bottle support
4 Controller
Cx Axis
CAM1 Camera
LED1, LED2 Illuminating unit

The invention claimed is:

1. A glass bottle inspection method for detecting a defect at a specific location of a glass bottle by producing a template serving as a reference image based on images of a defect-free glass bottle which have been captured previously using an illuminating unit and a camera, and by comparing an image of the glass bottle to be inspected with the template, the glass bottle inspection method comprising:

successively producing differential images from original images which are successively captured from the glass bottle to be inspected while the glass bottle is being rotated about its own axis;

comparing said differential images with said template to judge whether the glass bottle is defect-free or not, and combining all the differential images obtained from the glass bottle to be inspected in one inspection cycle to produce a differential composite image;

using said differential composite image as a provisional template when all the differential images obtained from the glass bottle in one inspection cycle are judged as representing a defect-free glass bottle; and correcting said template using said provisional template.

2. A glass bottle inspection method for detecting a defect at a specific location of a glass bottle by producing a template serving as a reference image based on images of a defect-free glass bottle which have been captured previously using an illuminating unit and a camera, and by comparing an image of the glass bottle to be inspected with the template, the glass bottle inspection method comprising:

judging whether the glass bottle is defect-free or not by comparing original images which are successively captured from the glass bottle to be inspected while the glass bottle is being rotated about its own axis or comparative images produced from said original images, with said template, and combining all the original images or all the comparative images obtained from the glass bottle to be inspected in one inspection cycle to produce a composite image;

using said composite image as a provisional template when all the original images or all the comparative images obtained from the glass bottle in one inspection cycle are judged as representing a defect-free glass bottle; and correcting said template using said provisional template.

3. A glass bottle inspection method according to claim 1, wherein said template is produced by successively producing differential images from original images which are successively captured from a predetermined number of defect-free glass bottles, and by superposing the produced differential images.

4. A glass bottle inspection method according to claim 1, wherein said template is corrected by combining said provisional template as additional data with said template.

5. A glass bottle inspection method according to claim 1, wherein said defect at the specific location of the glass bottle comprises a check in the bottle-mouth portion.

6. A glass bottle inspection apparatus for detecting a defect at a specific location of a glass bottle by producing a template serving as a reference image with an image processor which processes images of a defect-free glass bottle which have been captured previously using an illuminating unit and a camera, and by comparing an image of the glass bottle to be inspected with the template, wherein said image processor is configured to perform:

successively producing differential images from original images which are successively captured from the glass bottle to be inspected while the glass bottle is being rotated about its own axis;

comparing said differential images with said template to judge whether the glass bottle is defect-free or not, and combining all the differential images obtained from the glass bottle to be inspected in one inspection cycle to produce a differential composite image;

using said differential composite image as a provisional template when all the differential images obtained from the glass bottle in one inspection cycle are judged as representing a defect-free glass bottle; and correcting said template using said provisional template.

7. A glass bottle inspection apparatus for detecting a defect at a specific location of a glass bottle by producing a template serving as a reference image with an image processor which processes images of a defect-free glass bottle which have been captured previously using an illuminating unit and a camera, and by comparing an image of the glass bottle to be inspected with the template, wherein said image processor is configured to perform:

judging whether the glass bottle is defect-free or not by comparing original images which are successively captured from the glass bottle to be inspected while the glass bottle is being rotated about its own axis or comparative images produced from said original images, with said template, and combining all the original images or all the comparative images obtained from the glass bottle to be inspected in one inspection cycle to produce a composite image;

using said composite image as a provisional template when all the original images or all the comparative images obtained from the glass bottle in one inspection cycle are judged as representing a defect-free glass bottle; and correcting said template using said provisional template.

8. A glass bottle inspection apparatus according to claim 6, wherein said template is produced by successively producing differential images from original images which are successively captured from a predetermined number of defect-free glass bottles, and by superposing the generated differential images.

9. A glass bottle inspection apparatus according to claim 6, wherein said template is corrected by combining said provisional template as additional data with said template.

10. A glass bottle inspection apparatus according to claim 6, wherein said defect at the specific location of the glass bottle comprises a check in the bottle-mouth portion.

* * * * *